United States Patent [19]

Sudo et al.

[11] Patent Number: 4,975,366

[45] Date of Patent: Dec. 4, 1990

[54] MULTI-LAYERED ELEMENT FOR QUANTITITATIVE ANALYSIS OF IMMUNO REACTANT

[75] Inventors: Yukio Sudo; Nobuhito Masuda; Kenji Miura, all of Asaka, Japan

[73] Assignee: Fuji Photo Film Co., Ltd., Kanagawa, Japan

[21] Appl. No.: 15,916

[22] Filed: Feb. 18, 1987

[30] Foreign Application Priority Data

Feb. 20, 1986 [JP] Japan ................................. 61-33988

[51] Int. Cl.$^5$ ..................... G01N 21/78; G01N 33/53
[52] U.S. Cl. .......................................... 435/7; 422/56; 436/514; 436/170; 436/810; 435/805
[58] Field of Search ..................... 436/514, 170, 810; 435/7, 805; 422/56, 57

[56] References Cited

U.S. PATENT DOCUMENTS

| | | | |
|---|---|---|---|
| 3,992,158 | 11/1976 | Przybylowicz et al. | 422/57 |
| 4,258,001 | 3/1981 | Pierce et al. | 435/7 X |
| 4,806,312 | 2/1989 | Greenquist | 422/56 |

FOREIGN PATENT DOCUMENTS

| | | | |
|---|---|---|---|
| 0051183 | 5/1982 | European Pat. Off. | 436/170 |
| 0066648 | 12/1982 | European Pat. Off. | |
| 0119623 | 9/1984 | European Pat. Off. | |
| 3227474 | 2/1983 | Fed. Rep. of Germany . | |
| 8602165 | 4/1986 | PCT Int'l Appl. | |

OTHER PUBLICATIONS

Patent Abstracts of Japan, vol. 9, No. 210 P-383 [1933] Aug. 1985, JP-A-60-71954.

Primary Examiner—Robert J. Hill, Jr.
Attorney, Agent, or Firm—McAulay Fisher Nissen & Goldberg

[57] ABSTRACT

A multi-layered element for the quantative analysis of an immuno-reactant having a water-impermeable and light-transmissible support layer; a coloring reagent layer carried by said support layer and containing a hydrophilic polymer as a binder; and a reaction layer covering said reagent layer and made of a porous matrix. When the analyte immunoreactant is an antigen, said reaction layer contains the specific antibody for the antigen, the antibody being immobilized by a first water-insoluble carrier. When the analyte immuno-reactant is an antibody, said reaction layer contains the specific antigen for the antibody. The reaction layer contains an enzyme substrate immobilized by a second water-insoluble carrier different from said first water-insoluble carrier. The coloring reagent layer contains a detection reagent composition for coupling with an enzymatic reaction product produced by the reaction beween the enzyme-labelled complex of the immuno-reactant and the enzyme substrate immobilized by the second water-insoluble carrier. Upon coupling of the detection reagent composition with the enzymatic reaction product, a color is developed, the optical density of which is measured to determine the quantity of the analyte immuno-reactant contained in a liquid sample.

24 Claims, 2 Drawing Sheets

MULTI-LAYERED ELEMENT FOR QUANTITITATIVE ANALYSIS OF IMMUNO REACTANT

BACKGROUND OF THE INVENTION

1. Field of the Invention

The present invention relates to a multi-layered element for quantitative analysis of immuno-reactants, such as antigens and antibodies.

2. Related Art Statement.

The antigen-antibody reaction is an immuno-reaction in which an antigen reacts with the specific antibody to be combined together, and has been widely used in the clinical examinations for detecting a trace substance in a living body and for diagnosing an autoimmune disease. However, these examinations require skilled operations, and there is a demand for a simpler method for conducting a routine examination at an adequate reproducibility. It is also demanded that a small quantity of a sample can be analyzed within a short time preferably through an automated operation for a mass examination.

Japanese Patent Laid-Open Publication Nos. 200862/1982 (EP66648A) and 77356/1984 (EP101945A) disclose multi-layered elements for the simple and automatic quantitative analyses of antigens. Japanese Patent Laid-Open Publication No. 200862/1982 discloses a multi-layered element for the analysis of an antigen, which comprises a reaction layer containing the immobilized antibody for an antigen to be analyzed, and a detection layer composed of a hydrophilic polymer. When a mixture of the analyte antigen and a predetermined amount of the labelled antigen is added to the reaction layer, competitive antigen-antibody reactions take place in the reaction layer so that the antigen and the labelled antigen, which have not been combined with the immobilized antibody, migrates into the detection layer. The amount of the labelled antigen migrating into the detection layer is detected optically to determine the amount of the antigen contained in the analyte.

The multi-layered analysis element disclosed by Japanese Patent Laid-Open Publication No. 77356/1984 comprises a spreading layer containing a fluorescence-labelled antigen, a developing layer made of a porous matrix of high liquid-retention capacity, and a reaction layer containing an immobilized antibody. When the analyte antigen is added dropwise to the spreading layer, the antigen travels to the developing layer together with the fluorescence-labelled antigen contained in the spreading layer to be retained by the developing layer. If the reaction layer does not contain the immobilized antibody, the analyte antigen and the labelled antigen can migrate only in proportion to the ratio of the liquid-retention capacity of the developing layer to that of the reaction layer. However, since the reaction layer contains the immobilized antibody, the amounts of the analyte antigen and the labelled antigen migrating into the reaction layer are increased by the amounts thereof combined with the immobilized antibody. Accordingly, as the result of competitive antigen-antibody reactions of the analyte antigen and the labelled antigen, the quantity of the analyte antigen is determined as the function of the decrease in fluorescent light intensity of the reaction layer.

The aforementioned multi-layered analysis elements are epoch-making ones since the analysis operations can be simplified, and the automated operation can be provided thereby. However, since the dye or fluorescent dye label of the antigen are directly detected in these known elements, the detection sensitivities thereof are limited in principle.

In order to improve the detection sensitivity, it could be conceived by an application of enzymeimmunoassay. In such a method, an antigen (or antibody) is labelled by an enzyme and the activity of the enzyme labelling of the antigen (or antibody) which has been combined (or not combined) with its antibody (or antigen) through the competitive antigen-antibody reaction is detected. However, in such a method, the enzyme-labelled antigen (B) combined with antibody must be separated from the enzyme-labelled antigen (F) which has not been combined with the antibody (through a so-called B/F separation), or it is necessary to use an enzyme system having an activity for B which is different from that for F.

A system which does not require the B/F separation has been known by Japanese Patent Laid-Open Publication No. 2997/1980 (US 4,238,565), in which what is utilized is a phenomenon that the chemical affinity of the coenzyme with the apoenzyme is lowered by the coupling of the antibody with an antigen which has been preliminarily combined with the coenzyme. Japanese Patent Laid-Open Publication No. 209994/1983 (EP 94,777A) teaches a method wherein depression or enhancement in enzyme activity is utilized for quantitative analysis. In this known method, an enzyme-labelled antigen is used and coupled with an enzyme inhibitor or an enzyme activator. An enzyme and a specific antibody for the analyte antigen is carried by the same carrier to be immobilized thereby. The enzyme and the specific antibody may be carried by a relatively large particle at spatially separated sites, or may be carried by separated particles of the same carrier material. As the result of competitive reactions, the enzyme inhibitor or enzyme activator combined with the immobilized enzyme inhibits or activates the immobilized enzyme, so that the enzyme activity of the entire system is depressed or enhanced. By measuring the depression or enhancement factor of the enzyme activity, the analyte antigen is quantitatively analyzed.

However, the sensitivities of the known enzymeimmunoassay methods are low in principle, since the quantity of the analyte unlabelled antigen is determined by the ratio of inhibition or activation of the enzyme activity. These methods have the disadvantages that the times for the enzymatic reactions must be prolonged for improving the sensitivities.

Accordingly, there is a demand for a multi-layered analysis element in which the enzymeimminoassay is applied and in which the B/F separation can be substantially realized for carrying out the quantitative analysis in a short time and at a high sensitivity.

OBJECT AND SUMMARY OF THE INVENTION

Accordingly, the object of this invention is to provide a multi-layered element for the quantitative analysis of an immuno-reactant, such as an antigen or an antibody, with the use of a small quantity of the analyte immuno-reactant sample in a simple manner and a short time at a high sensitivity.

Another object of this invention is to provide such a multi-layered element for the quantitative analysis of an immuno-reactant that it may be used in an automated analysis operation.

In order to achieve the aforementioned objects, the analyte immuno-reactant (antigen or antibody) is allowed to react with the corresponding immuno-reactant (antibody or antigen) in competition with the reaction between the enzyme-labelled immuno-reactant and the corresponding immuno-reactant in a reaction layer, in which the corresponding immuno-reactant (antibody or antigen) is immobilized by a carrier, and an enzyme substrate is immobilized by another carrier, so that only the complex of the analyte immuno-reactant and the enzyme which has not been combined with the immobilized corresponding immuno-reactant is allowed to react with the immobilized enzyme substrate to move the reaction product of the enzymatic reaction to a reagent layer to be detected by coloring under the action of the coloring reagent.

According to one aspect of this invention, it provided a multi-layered element for the quantitative analysis of an analyte antigen, said analyte antigen being mixed with an enzyme-labelled antigen, comprising: a water-impermeable and light-transmissible support; a reagent layer carried by said support and containing a hydrophilic polymer as a binder; and a reaction layer covering said reagent layer and made of a porous matrix; said reaction layer containing an antibody for the antigen and a substrate for the enzyme labelling to said antigen, said antibody being immobilized by a first water-insoluble carrier, said substrate being immobilized by a second water-insoluble carrier which is different from said first water-insoluble carrier for immobilizing said antibody, a part of said enzyme-labelled antigen being combined with the immobilized antibody to be fixed thereby and the remaining part of said enzyme-labelled antigen reacting with the immobilized substrate to produce an enzymatic reaction product; said reagent layer containing a detection reagent composition for coupling with said enzymatic reaction product to develop a color.

According to another aspect of this invention, it provided a multi-layered element for the quantitative analysis of an analyte antibody, said analyte antibody being mixed with an enzyme-labelled antibody, comprising: a water-impermeable and light-transmissible support; a reagent layer carried by said support and containing a hydrophilic polymer as a binder; and a reaction layer covering said reagent layer and made of a porous matrix; said reaction layer containing an antigen for the antibody and a substrate for the enzyme labelling to said antibody, said antigen being immobilized by a first water-insoluble carrier, said substrate being immobilized by a second water-insoluble carrier which is different from said first water-insoluble carrier for immobilizing said antigen, a part of said enzyme-labelled antibody being combined with the immobilized antigen to be fixed thereby and the remaining part of said enzyme-labelled antibody reacting with the immobilized substrate to produce an enzymatic reaction product; said reagent layer containing a detection reagent composition for coupling with said enzymatic reaction product to develop a color.

In a preferred embodiment, the analyte antigen or antibody is mixed with the enzyme-labelled antigen or enzyme-labelled antibody contained in the reaction layer or the reagent layer.

DESCRIPTION OF THE INVENTION

In the reaction layer of the multi-layered analysis element of this invention, the immobilized immuno-reactant molecules (antibody or antigen) are spatially separated from the immobilized enzyme substrate molecules. Therefore, when a certain enzyme-labelled immuno-reactant molecule (antigen or antibody) is coupled with the immobilized corresponding immuno-reactant molecule (antibody or antigen), the enzyme thereof cannot attack the immobilized enzyme substrate molecule and can no longer participate in any enzymatic reaction. When analyte immuno-reactant molecules (which are not labelled by any enzymes) are added simultaneously, the molecules of the enzyme-labelled immuno-reactant can attack the immobilized enzyme substrate molecules through an enzymatic reaction to produce enzymatic reaction product molecules which move or penetrate into the detection layer (the reagent layer) containing a coloring reagent. The color developed by the reagent is colorimetrically determined through the light-transmissible support.

First Embodiment of the Invention

Figure 1:
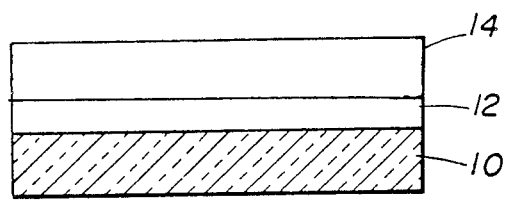
FIG. 1 is a sectional view showing an embodiment of the multi-layered element for the quantitative analysis according to this invention.

A first embodiment of the multi-layered element for the quantitative analysis, according to this invention, will now be described with reference to FIG. 1 showing the cross section thereof.

A light-transparent support is denoted by reference numeral 10, on which overlaid is a coloring reagent layer 12 made of a hydrophilic polymer. A reaction layer 14 made of a porous matrix is overlaid on the coloring reagent layer 12. The reaction layer 14 contains an antibody for the analyte antigen, the antibody being immobilized by a first water-insoluble carrier, and an enzyme substrate immobilized by a second water-insoluble carrier different from the first water-insoluble carrier for immobilizing said antibody. The coloring reagent layer 12 contains a reagent for detecting the product of the enzymatic reaction taking place in the reaction layer 14 to develop a color. The reaction layer 14 of this embodiment further contains dispersed micro particles of rutile type or anatase type, titanium oxide, for shielding the color.

The enzyme substrate contained in the reaction layer 14 and the detection reagent contained in the coloring reagent layer 12 may be selected in consideration of the analyte antigen and the enzyme dropped onto the multi-layered element. In detail, the combination of the enzyme, the enzyme substrate and the detection reagent is properly selected so that the quantity of the product by the enzymatic reaction is determined by the quantity of the colored dye.

Although the aforementioned embodiment has been described as it is used for the analysis of an antigen, the multi-layered element of this invention can be modified to use for the analysis of an antibody. In such a modified embodiment, the reaction layer 14 contains an antigen for the analyte antibody, and the antigen contained in the reaction layer 14 is immobilized by a water-insoluble carrier.

The components constituting respective layers of the multi-layered element of this invention will now be described in detail.

Support

The support 10 may be made of a water-impermeable and light-transmissible (transparent) material which transmits an electromagnetic radiation having a wavelength within the region between about 200 nm and about 900 nm. Examples of the material which may be used as the support 10 are selected from the known supports made of a film, sheet or flat plate having a smooth surface and made of a polymer material, such as polyethyleneterephthalate, polycarbonate of bisphenol-A, polystyrene, and cellulose esters including cellulose diacetate, cellulose triacetate and cellulose acetate propionate. The thickness of the support may range from from 50 microns to about 1 mm, preferably from about 80 microns to about 300 microns.

The support 10 may contain micro particles of titanium dioxide, barium sulfate and/or carbon black dispersed uniformly therein to have an adjusted optical property, as desired. The surface of the support 10 may be applied with a known undercoat to ensure strong adhesion between the support 10 and the coloring reagent layer 12.

Porous Matrix

The porous matrix constituting the reaction layer 14 may be any material which does not substantially react with the antigen, antibody, and enzyme in the sample liquid dropped thereto, and which can retain the carriers immobilizing the antibody (or antigen) and the enzyme substrate. The preferred materials are fibrous and non-fibrous porous sheets.

Examples of the fibrous porous sheets are woven fabrics, knitted fabrics, paper and filter paper containing an organic polymer fiber pulp, paper and filter paper containing glass fiber pulp, and non-woven cloth of fibers.

The plain weaves for the spreading layers disclosed in Japanese Patent Laid-Open Publication Nos. 164356/1980(US 4,292,272) and 222770/1985 (EP 162,301A) are preferable fabric cloths, particularly preferred plain weaves being a thin cloth, calico cloth, broad cloth, poplin cloth. The woven cloths are preferably made of spun yarns (threads). The thickness of the yarns for the woven cloths range from about 20S to about 150S, preferably from about 40S to about 120S, when identified by the cotton yarn count, and range from about 45D to about 300D, preferably from about 45D to about 130D, when identified by the silk denier. The thickness of the woven cloth ranges from about 100 microns to about 500 microns, preferably from about 120 microns to about 350 microns. The porosity of the woven cloth ranges from about 40% to about 90%, preferably from about 50% to about 85%.

A preferred knitted cloth is a lengthwise knitted cloth disclosed in Japanese Patent Laid-Open Publication Nos. 222769/1985 (EP 162,302A) and 222770/1985 (EP 162,301A) as forming the spreading layer, particularly preferred lengthwise knitted cloths being tricot knitted cloth, Raschel stitch knitted cloth, Milanese stitch knitted cloth and double-tricot knitted cloth. It is preferable that the knitted cloth is composed of spun yarns (threads). The thickness of the yarns for the knitted cloths ranges from about 40S to about 150S, preferably from about 60S to about 120S, when identified by the cotton yarn count, and ranges from about 35D to about 130D, preferably from about 45D to about 90D, when identified by the silk denier, and ranges from about 20 to about 50 when identified by the gage number at the knitting step for producing the knitted cloth. The thickness of the knitted cloth ranges from about 100 microns to about 600 microns, preferably from about 150 microns to about 400 microns. The porosity of the knitted cloth ranges from about 40% to about 90%, preferably from about 50% to about 85%.

The fibrous materials which may be used for the preparation of paper, filter paper and non-woven cloths include inorganic fibers, such as glass fibers and asbestos, natural organic fibers, such as cotton, hemp and silk, and semi-synthetic and synthetic fibers, such as copper-ammonia rayon, cellulose acetate, partially formalized polyvinylalcohol, polyethylene and polyesters including polyethylene terephthalate.

It is preferred that the fibrous material has a thickness of from 0.1 to 5 microns and a length of from 500 to 4000 microns.

Examples of preferable paper containing an organic polymer fiber pulp are paper composed solely of polyethylene fibers as disclosed, for example, by Japanese Patent Laid-Open Publication No. 148250/1982, paper made of a mixed pulp of a natural fibers with polyethylene fibers (30 to 70%) and paper made of cellulose fibers. The thickness of the paper may range from about 80 to about 400 microns, preferably from about 100 to about 250 microns; and the porosity thereof ranges from about 20% to about 80%, preferably from about 50% to about 70%.

When the fiber base porous sheet is a woven or knitted cloth (the woven and knitted cloths being referred to generally and simply as "cloth" or "cloths" in some portions), it should be substantially deprived of the oils and fats adhering at both or either one of the yarn making step and cloth fabricating step through a dewaxing treatment, for example, by rinsing with water or a solvent. Paper and filter paper which may be used as the porous matrix in this invention should be substantially free from oils and fats. One or both of the surfaces of the fiber base porous sheet may be subjected to a physical activation treatment, preferably glow discharge processing or corona discharge processing, disclosed in Japanese Patent Laid-Open Publication No. 66359/1982 (GB 2,087,074A); or the fiber base porous sheet may be impregnated, coated or sprayed with an aqueous solution of a surfactant, preperably a nonionic surfactant, as disclosed in Japanese Patent Laid-Open Publication Nos. 164356/1980, 66359/1982 and 148250/1982.

As a porous sheet made of a non-fibrous material and preferably used in this invention, it may be mentioned to a non-fibrous isotropic porous sheet, the examples being a membrane filter (blush polymer layer) made of a cellulose ester such as cellulose acetate, a polyamide such as Nylon-6 or Nylon-66, or a polycarbonate of bisphenol-A as disclosed by Japanese Patent Publication No. 21677/1978 and U.S. Pat. Nos. 1,421,341 and 3,992,158; polyolefin microporous membranes such as polyethylene microporous membrane and polypropylene microporous membrane as disclosed in the "Dai-9 Kai Plastic Film Kenkyukai Kouza Koen Yoshishu" (Collection of Summary of Report in the Ninth Plastic Film Research Meeting) (published by Kobunshi Gakkai (Japan Polymer Science Society), on Feb. 22, 1984) and the catalogue published by the Membrane, Inc., in July of 1982; a porous sheet containing open cellular micropores composed of micro particles, such as polymer microbeads, glass microbeads or diatomaceous earth retained by a hydrophilic polymer binder as disclosed by Japanese Patent publication No. 21677/1978 and U.S. Pat. No. 3,992,158; a porous sheet containing open cellular micropores (three-dimensional lattice structure of particles) made of polymer microbeads bound through point contact by a polymer adhesive which is not swelled by water as disclosed by Japanese Patent Laid-Open publication No. 90859/1980 (US 4,258,001).

The pore size of the non-fibrous porous sheet ranges generally from about 20 nm to about 30 microns, preferably from about 50 nm to about 10 microns; the porosity thereof ranges generally from about 20% to about 90%, preferably from about 40% to about 85%; and the thickness thereof ranges generally from about 20 microns to about 500 microns, preferably from about 80 microns to about 350 microns.

The non-fibrous porous sheet may contain light-shielding and/or light-reflecting microparticles as disclosed in Japanese Patent publication No. 21677/1978, U.S. Pat. No. 3,992,158 and Japanese Patent Laid-Open Publication No. 90859/1980 in order to exclude optical interference in reflected light intensity measurement due to the presence of red hemoglobin in the whole blood. When a three-dimensional lattice structure of particles is used, light-shielding and/or light-reflecting microparticles may be incorporated by point contact into the three-dimensional particle structure by a binder. Examples of the light-shielding and/or light-reflecting microparticles are microparticles of titanium dioxide, microparticles of barium sulfate, carbon black, and microparticles of aluminium or micro-flakes thereof. Microparticles of titanium dioxide and microparticles of barium sulfate are preferred.

The non-fibrous porous sheet may be impregnated with a known surfactant, preferably with a nonionic surfactant, to uniformalize the dispersion, permeation and passage of an aqueous liquid sample.

Carrier

The carrier for immobilizing the antibody or the enzyme substrate may be any known material, as far as it is water-insoluble, does not influence the antigen-antibody reaction, and the enzymatic reaction and has a functional group for immobilizing the antibody or the enzyme substrate or a site on which such a functional group can be introduced.

Examples of such a carrier include polysaccharides, such as agar, agarose and dextran; latexes prepared by polymerization or copolymerization of an acrylamide or polymerizable ethylenic monomers; and non-fibrous microparticles, such as cellulose powder. Non-fibrous microparticle materials, such as agar and agarose, are preferred, since the volume of liquid retained thereby per a unit thickness of the reaction layer is increased.

A fibrous material may be used for serving as the carrier, and a paper sheet is prepared from the fibrous material to use as a porous sheet forming the reaction layer 14.

The carrier may be bonded or fixed to the antibody or the enzyme substrate through the known technology disclosed, for example, by Japanese Patent Laid-open Publication Nos. 7237/1978, 7238/1978 and 7239/1978 and U. S. Pat. No. 4,168,164. The methods for bonding or fixing the carrier to the antibody or the enzyme substrate include a process including acylation by processing with carbonyl diimidazole, a process including activation with CNBr (bromocyane) and a process including processing with a functional cross-linking agent such as glutaraldehyde.

Antibody

The specific antibody for the analyte antigen should be used. The antibody prepared by the ordinary manner may be used, and the sensitivity of the element may be improved by the use of the monoclonal antibody.

Coloring Reagent Layer

The coloring reagent layer 12 is a layer containing, as the binder ingredient, a hydrophilic polymer which absorbs water to be swelled thereby, and a detection reagent which detects the product of enzymatic reaction taking place in the reaction layer 14 to develop a color. This coloring reagent layer also serves as a water-absorbing layer.

The hydrophilic polymer which may be used in the reagent layer has a percentage swelling generally ranging from about 150% to about 2000%, preferably from about 250% to about 1500%. Specific examples of the hydrophilic polymer used in this invention include gelatines, such as a gelatine treated with an acid and a deionized gelatine, gelatine derivatives, such as a phthalated gelatine and a hydroxyacrylate graft gelatine, as disclosed by Japanese Patent Laid-Open Publication Nos. 171864/1984 (EP 119,861A) and 115859/1985; and agarose, pururan, pururan derivatives, polyacrylamides, polyvinyl alcohol and polyvinyl pyrrolidone as disclosed by Japanese Patent Laid-Open Publication Nos. 171864/1984 and 115859/1985. These hydrophilic polymers may be used singly or in combination with one or more other hydrophilic polymers. In general, it is preferred that the coloring reagent layer contains gelatine or a gelatine derivative. However, when the analyte is an antibody or an antigen which is a protein, it is preferred that the reagent layer contains a hydrophilic polymer, such as polyacrylamides or polyvinyl alcohol, rather than using gelatine which is a derivative of protein.

The dry coloring reagent layer has a thickness generally ranging from about 3 microns to about 50 microns, preferably from about 5 microns to about 30 microns, and is coated in a coating amount of from about 3 g/m$^2$ to about 50 g/m$^2$, preferably from about 5 g/m$^2$ to about 30 g/m$^2$. The coloring reagent layer may contain a known pH buffer, an organic carboxylic acid, an acidic polymer or a basic polymer to have an adjusted pH value at use (during the analytical operation). The coloring reagent layer may be further added with a known mordant or polymer mordant. Although it is preferred that the coloring reagent layer is substantially transparent, a small amount of microparticles of titanium dioxide, microparticles of barium sulfate or carbon black may be dispersed in the coloring reagent layer to control the optical property of the layer, if necessary.

A water-absorbing layer may be interposed between the coloring reagent layer 12 and the support 10. The water-absorbing layer may be mainly composed of a hydrophilic polymer similar to the coloring reagent layer. The dry water-absorbing layer has a thickness generally ranging from about 1 micron to about 100 microns, preferably from about 3 microns to about 30 microns so that the coating amount ranges generally from about 1 g/m$^2$ to about 100 g/m$^2$, preferably from about 3 g/m$^2$ to about 30 g/m$^2$. The water-absorbing layer may contain a known pH buffer, an organic carboxylic acid, an acidic polymer or a basic polymer to have an adjusted pH value at use (during the analytical operation). The water-absorbing layer may contain a mordant, a polymer mordant, a basic polymer or an acidic polymer to serve as a detection layer.

Enzyme-Enzyme Substrate-Detection Reagent

The enzyme substrate contained in the reaction layer 14 and the detection reagent contained in the coloring reagent layer should be selected in relation to the enzyme labelling to the analyte antigen to be analyzed by the multi-layered element of this invention. Namely, a special combination of the enzyme, enzyme substrate and detection reagent is used such that the quantity of the product of the enzymatic reaction is detected as the factor of the coloring pigment produced under the action of the used detection reagent.

Detection Reagent Example 1

When the antigen is labelled by $\beta$-D-galactosidase and a galactose oligomer is used as the enzyme substrate, a combination of galactose oxidase, peroxidase and a coloring reagent composition may be used as the detection reagent. Galactose oxidase dehydrates D-galactose, which is a product (decomposition product) of the enzymatic reaction of galactose oligomer to produce $H_2O_2$ as a by-product. Under the action of peroxidase, $H_2O_2$ reacts with the coloring reagent composition to produce a coloring matter (pigment). Although galactose oxydase also reacts with the galactose oligomer, the galactose oligomer does not hinder detection of D-galactose in the coloring reagent layer. This is because the galactose oligomer, which is present as the immobilized enzyme substrate in the reaction layer 14, is separated from the galactose oxidase in the coloring reagent layer.

$\beta$-D-galactosidase (EC 3.2.1.23) described in "Rinsho Koso Handbook" (Clinical Enzyme Handbook) edited by Baba, Wada, Kitamura and Okuda, Kodansha (1982) and T.E. Barman, "Enzyme Handbook", Springer Verlag (1969) may be used as the $\beta$-D-galactosidase for labelling the antigen. Particularly preferable $\beta$-D-galactosidase is that originated from *Diplococcus pneumoniae*.

Galactose oxidase (EC 1.1.1.48) originated from a microorganism, such as *Polyporus circinatus* or *Dactylium dendoroides*, as described in "Rinsho Koso Handbook" (Clinical Enzyme Handbook) edited by Baba, Wada, Kitamura and Okuda, Kodansha (1982), "Koso Handbook" (Enzyme Handbook) edited by Maruo and Tamiya, Asakura-shoten (1982) and T. E. Barman, "Enzyme Handbook", Springer Verlag (1969) may be used as the galactose oxidase in the multi-layered element of this invention. The galactose oxidase may be used together with a coenzyme thereof or with $Cu^{2+}$ ions, if necessary. A known pH buffer may be contained in the layer containing the galactose oxidase or the adjacent layer so that the pH value of the layer is maintained within the range of from pH 6.5 to pH 8.0, preferably from pH 6.8 to pH 7.5 during the analyzing operation. The content of galactose oxidase contained in 1 $m^2$ of the multi-layered element is controlled within the range of from about 1,000 U to about 100,000 U, preferably from about 2,000 U to about 50,000 U.

Examples of the peroxidase which may be used in the multi-layered element of this invention are a peroxydase (EC 1.11.1.7) originated from a vegetable or an animal as described in "Rinsho Koso Handbook" (Clinical Enzyme Handbook) edited by Baba, Wada, Kitamura and Okuda, Kodansha (1982), "Koso Handbook" (Enzyme Handbook) edited by Maruo and Tamiya, Asakura-shoten (1982), T. E. Barman, "Enzyme Handbook", Springer Verlag (1969) and Japanese Patent Publication Nos. 45599/1981 and 5520/1982 (US 4,211,845), and a peroxydase (EC 1.11.1.7) originated from a microorganism as described in Japanese Patent publication No. 5035/1983. It is preferred that a non-specific peroxidase originated from a vegetable or a microorganism is used. Examples of preferred peroxidase are horse radish peroxidase, radish peroxidase and peroxidase extracted from microorganisms of Cochliobulus and Curvularia genera.

A known pH buffer may be contained in the layer containing the peroxidase or the adjacent layer so that the pH value of the layer is maintained within the range of from pH 5.0 to pH 8.0, preferably from pH 6.0 to pH 7.0 during the analyzing operation. The content of peroxidase contained in 1 $m^2$ of the multi-layered element is controlled within the range of from about 1,000 U to about 100,000 U, preferably from about 2,000 U to about 60,000 U.

If necessary, the peroxidase may be used together with a compound containing hexacyanoferric (II) ions or a compound which can release hexacyanoferric (II) ions as described in Japanese Patent Publication No. 25840/1980 (US 3,886,045).

The coloring reagent composition, which may be used in this invention, forms a coloring matter (pigment) in the presence of $H_2O_2$ and peroxidase, the examples being those containing pigments colored by oxidation (leuco-pigments) as disclosed by Japanese Patent Publication Nos. 45599/1981 (US 3,983,005) and 18628/1983 (US 4,042,335); those forming coloring matters (pigments) by oxidation coupling as disclosed by "Annales of Clinical Chemistry", 6, pages 24 to 27 (1969), U.S. Pat. No. 3,992,158, Japanese Patent Publication Nos. 25840/1980, 45599/1981 and 18628/1983 and Japanese Patent Laid-Open Publication No. 54962/1984 (EP 103,901A); and pigment precursors colored or discolored by autocoupling as disclosed by Japanese Patent Publication Nos. 45599/1981 and 18628/1983.

The following are examples of the preferable coloring reagent composition:

Combination of a hydrogen donor (chromogen) and a coupler

Hydrogen Donor: 4-Aminoantipyrine homologue and derivatives thereof, such as 4-aminoantipyrine and 4-amino-2-methyl-3-phenyl-1-(2,4,6-trichloro phenyl)-3-pyrazoline-5-one Coupler: Derivatives of 1-hyroxynaphthalene, such as 1,7-Dihydroxynaphthalene and sodium (or potassium) 1-hydroxynaphthalene-2-sulfonate Triarylimidazole Base Leuco-Pigment 4,5-Bis(4-(diethylamino)phenyl)-2-(4-hydroxy-3,5-dimethoxyphenyl)imidazole 4-(Dimethylamino)phenyl-2-(4-hydroxy-3,5-dimethoxyphenyl)-5-phenetylimidazole Pigment Precursor Dianisidine and 4-methoxy-1-naphtol Detection Reagent Example 2

Another example of the detection reagent which may be used in this invention is a combination of galactose dehydrogenase, NAD and a reagent for detecting NADH. Galactose dehydrogenase dehydrogenates D-galactose which is a decomposition product of the immobilized enzyme substrate to reduce NAD to NADH. Accordingly, by the determination of the decrement of NAD or by the determination of formed NADH, the quantity of the product of the enzymatic reaction of the labelling enzyme can be measured.

Examples of the coloring reagent composition for colorimetric determination of NAD or NADH are coloring reagent compositions for determining the lactate dehydrogenase activity as described in Clinica Chimica Acta, 12, 210 (1965) and Japanese Patent Laid-Open Publication Nos. 44658/1984 and 88097/1984; coloring reagent compositions for determining aspartate-amino-transferase activity and coloring reagent compositions for determining alanine-amino-transferase activity as described in Clinica Chimica Acta, 28, 431 (1970) and Japanese Patent Laid-Open Publication Nos. 44894/1985, 208998/1982, 44658/1984 and 88097/1984; a coloring reagent composition for determining creatine-kinase activity as described in Japanese Patent publication No. 9988/1971; coloring reagent compositions for determining creatine-phospho-kinase activity as described in Japanese Patent Laid-Open Publication Nos. 11395/1974 (US 3,663,374), 44658/1984 and 88097/1984; coloring reagent compositions for determining testosterone activity and coloring reagent compositions for determining andosterone activity as described in U.S. Pat. No. 3,791,933; coloring reagent compositions for determining amylase activity as described in Japanese Patent Publication No. 39637/1981(GB 1,590,738); coloring reagent compositions for analyzing glycerol as described in Japanese Patent Publication No. 21677/1978; and coloring reagent compositions for analyzing triglyceride as described in Japanese Patent Laid-Open Publication Nos. 126494/1975 (US 4,142,938) and 24893/1978 (GB 1,590,738) and Japanese Patent Publication No. 38199/1981 (US 4,273,870).

Amongst the coloring reagent compositions as set forth hereinabove, it is convenient to use the coloring reagent compositions for the colorimetric determination of the quantity of free NADH in accordance with the methods as disclosed by Japanese Patent Publication Nos. 38199/1981 and 46799/1981 (US 4,259,440) while using tetrazonium slats in the presence of diaphorase to produce formazan pigments.

Known galactose dehydrogenase (EC 1.1.1.48) and NAD may be used.

Detection Reagent Example 3

When the antigen is labelled by β-D-glucosidase and a glucose oligomer is used as the enzyme substrate, galactose oxidase used in the detection reagent examples 1 and 2 may be replaced by glucose oxidase to prepare a modified detection reagent composition.

In this modified composition, a known β-D-glucosidase (EC 3.2.2.21) may be used.

The most preferable glucose oligomer is an oligomer of β-D-glucose, and the next best glucose oligomer is 2-deoxy-D-glucose.

Examples of the glucose oxidase which may be used in this modified reagent composition are glucose oxidase (EC 1.1.3.4) originated from microorganisms, such as *Aspergillus niger, Penicillium notatum* and *Penicillium amagasakiense*, as described in "Rinsho Koso Handbook" (Clinical Enzyme Handbook) edited by Baba, Wada, Kitamura and Okuda, Kodansha (1982), "Koso Handbook" (Enzyme Handbook) edited by Maruo and Tamiya, Asakura-shoten (1982) and T. E. Barman, "Enzyme Handbook", Springer Verlag (1969). The glucose oxidase may be used together with a coenzyme FAD thereof and iron ions, as desired. A known pH buffer may be contained in the layer containing the glucose oxidase or the adjacent layer so that the pH value of the layer is maintained within the range of from pH 4.0 to pH 8.0, preferably from pH 5.0 to pH 6.5 during the analyzing operation. The content of glucose oxidase contained in 1 $m^2$ of the multi-layered element is controlled within the range of from about 1,000 U to about 100,000 U, preferably from about 2,000 U to about 50,000 U.

Detection Reagent Example 4

When the antigen is labelled by β-amylase (EC 3.2.1.2) and starch is used as the enzyme substrate, the coloring reagent composition for determining amylase activity, as described in Japanese Patent publication No. 39637/1981, may be used as the detection reagent.

When water-insoluble starch is used, the water-insoluble starch acts both as the carrier and as the immobilized enzyme susbtance. The present invention includes such a composition.

Buffer

The multi-layered element for quantitative analysis of immuno-reactant, according to this invention, may contain a buffer selected from the known buffers for controlling the pH values of the layers at a desired value ranging within pH 6.5 to pH 8.0, preferably from pH 7.0 to 7.5 during the analyzing step after the layers are applied with the liquid sample.

Examples of the pH buffer system which may be used in this invention are described in "Kagaku Binran, Kiso-hen" (Chemical Handbook, Fundamental Volume), edited by Chemical Society of Japan and published by Maruzen, Tokyo (1966), pages 1312 to 1320, "Data for Biochemical Research", Second Edition, edited by R. M. C. Dawson et al and published by Oxford at the Clarendon Press (1969), pages 476 to 508, "Biochemistry" 5, page 467 et seq (1966) and "Analytical Biochemistry", 104, pages 300 to 310 (1980).

Specific examples of the buffer for controlling the pH value within the range of from pH 4.5 to pH 8.0 are buffers containing tris(hydroxymethyl)aminomethane (Tris), buffers containing phosphates, buffers containing borates, buffers containing citric acid or citrates, buffers containing glycine, malic acid, succinic acid, malonic acid, tartaric acid, glutaric acid, 3,3-dimethylglutaric acid, N,N-bis(2-hydroxyethyl)glycine (Bicine), N-2-hydroxyethylpiperazine-N'-2-ethane sulfonic acid (HEPES), and combinations thereof with acids, alkalis and salts. Particularly preferred examples of the buffer are malic acid, succinic acid, tartaric acid, 3,3-dimethyl-glutaric acid, potassium dihydrogen phosphate-disodium hydrogenphosphate, Tris-sodium borate, Tris-sodium borate-disodium salt of EDTA, Tris-citric acid, acetic acid-sodium acetate, citric acid-sodium dihydrogenphosphate, Bicine and HEPES.

Preparation of Multi-Layered Element of the Invention

The dry multi-layered element for quantitative analysis of immuno-reactant, according to this invention, may be prepared through any of the known processes disclosed by the specifications of the preceding patents or patent applications referred to hereinbefore.

It is preferred for the convenience in preparation, package, transportation, storage and analytical operation that the multi-layered element of this invention is cut into 15 mm square to 30 mm square pieces or disks of substantially same size and each of the thus cut pieces is fixed on a slide frame disclosed, for example, by Japanese Patent Publication No. 28331/1982 (US 4,169,751), Japanese Utility Model Laid-Open Publication No. 142454/1981 (US 4,387,990), Japanese Patent Laid-Open Publication No. 63452/1982, Japanese Utility Model Laid-Open Publication No. 32350/1983 and Japanese Patent Laid-Open Publication No. 501144/1983 (WO 83/00391) to form a slide for chemical analysis. In some cases, it may be contained in a cassette or magazine to be applied for use in the form of an elongated tape, or a small piece thereof may be applied on or contained in a card having an opening.

Method of Quantitative Analysis of an Analyte by the Use of the Multi-Layered Element of the Invention The multi-layered element for quantitative analysis of immuno-reactant, according to this invention, may be used for the quantitative analysis of an analyte (antigen or antibody) contained in an aqueous liquid sample in a manner similar to the known methods disclosed by the specifications of the preceding patents or patent applications referred to hereinbefore.

The same antigen as that to be analyzed by the multi-layered element or an antigen having at least one common antigen determinant contained in the analyte antigen is prepared, and the thus prepared antigen is combined with an enzyme to prepare an antigen-enzyme complex. Such an antigen-enzyme complex may be produced by the prior art technology for combining the antigen with a carrier.

An aqueous solution of the antigen-enzyme complex is mixed with an aqueous liquid sample, such as whole blood, plasma or serum, containing the analyte antigen, and the mixed aqueous solution is spotted on the reaction layer 14 in an amount of from about 5 microliters to about 30 microliters, preferably from 8 to 15 microliters. The multi-layered element applied with a spot of the mixed aqueous solution is incubated at a constant temperature of from about 20° C. to about 40° C., preferably at about 37° C., whereby competitive antigen-antibody reactions take place in the reaction layer so that the immobilized enzyme substrate is decomposed by only the enzyme molecules combined with the antigen molecules which has not been combined with the antibody molecules. The product of the decomposition reaction penetrates and migrates into the coloring reagent layer 12 to react with the detection reagent to develop a color. The quantity of the antigen contained in the sample liquid can be determined by the principle of colorimetry by determining the optical density of the light reflected by the coloring matter (pigment) produced in the coloring reagent layer 12 through the light-transmissible support 14. Since color shielding microparticles are dispersed in the reaction layer 14 of this embodiment, the determination of the optical density of the reflected light is not interfered by colored particles, such as red blood cells, which they cannot penetrate into the coloring reagent layer, even if the sample liquid is a colored liquid, such as whole blood.

Second Embodiment of the Invention

Figure 2:
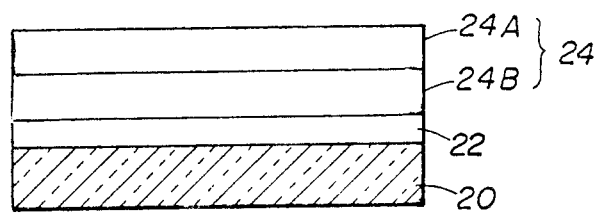
FIG. 2 is a sectional view showing another embodiment of the multi-layered element for the quantitative analysis according to this invention.

A second embodiment of the multi-layered element for quantitative analysis of an immuno-reactant, according to this invention, is shown in FIG. 2. In the second embodiment of this invention, the reaction layer 24 includes a first reaction layer 24A containing an antibody (antigen) immobilized by a first carrier, and a second reaction layer 24B containing an enzyme substrate immobilized by a second carrier. The second reaction layer 24B is overlaid on a coloring reagent layer 22 and the first reaction layer 24A is overlaid on the second reaction layer 24B. Coloring layer 22 is on a water-impermeable and transparent support 20.

In the first embodiment of this invention, the immobilized antibody (antigen) and the immobilized enzyme substrate are present in a single reaction layer 14, and a substantial B/F separation is realized since the chemical affinity between the antigen and its antibody is extremely greater than the chemical affinity between the enzyme and its substrate. Accordingly, in the first embodiment of this invention, a substantial B/F separation is the result of the fact that the enzyme-labelled antigen once combined with the immobilized antibody is scarcely separated from the immobilized antibody whereas the binding force between the immobilized enzyme substrate and the enzyme labelling to the antigen is not so strong as to hinder separation of the enzyme-labelled antigen.

In contrast to the first embodiment, only the antigen-enzyme complex molecules which have not been combined with the immobilized antibody molecules in the first reaction layer 24A are allowed to move into the second reaction layer 24B where they react with the immobilized enzyme substrate molecules contained in the second reaction layer 24B in this second embodiment. Accordingly, in the second embodiment of this invention, a physical B/F separation is achieved to result in more complete B/F separation as compared to the first embodiment in which the difference in chemical affinity is utilized, leading to further improvement in detection sensitivity.

The materials used for constituting the first embodiment of the multi-layered element of this invention may also be used in this second embodiment.

Third Embodiment of the Invention

The first embodiment may be modified by the provision of a reaction layer 14 containing an antigen-enzyme complex. By the use of such a modification, the aqueous liquid sample containing the analyte antigen may be simply spotted on the reaction layer 14 to determine the quantity of the analyte antigen in a simpler manner.

Since the reaction layer 14 is maintained in a dry condition before it is spotted with the aqueous liquid sample, the enzyme in the antigen-enzyme complex does not react with the immobilized enzyme substance in the dry reaction layer 14. When the reaction layer is divided into two separate layers, as in the case of the second embodiment where the reaction layer 24 includes the first reaction layer 24A and the second reaction layer 24B, it is preferred that the antigen-enzyme complex is contained only in the first reaction layer 24A which does not contain the immobilized enzyme substrate.

Fourth Embodiment of the Invention

The first embodiment may be modified by the provision of a coloring reagent layer 12 containing an antigen-enzyme complex.

In this modification, an aqueous liquid sample spotted on the reaction layer 14 penetrates into the coloring reagent layer 12, and the antigen-enzyme complex migrates from the coloring reagent layer 12 to the reaction layer 14. Accordingly, the analyte antigen contacts with the immobilized antibody before the enzyme-labelled antigen contacts with immobilized antibody so that reaction of the analyte antigen with the immobilized antibody takes place preferentially as in the case where competitive antigen-antibody reactions take place.

According to the fourth embodiment, in addition to simplification of the operation for determining the quantity of the analyte, the S/N ratio is improved and the analyte can be detected at a higher sensitivity.

Fifth Embodiment

According to a further modified embodiment of the invention, a spreading layer containing an antigen-enzyme complex may be overlaid on the reaction layer 14 or the first reaction layer 24A. By the provision of such a spreading layer, the analyte antigen need not be mixed with the enzyme-labelled antigen before the application thereof on the multi-layered element to realize the simplified analytical operation similar to the third and fourth embodiments.

The spreading layer provided for this purpose may be the one which exerts a spreading function or metering function for distributing the aqueous liquid sample spotted thereon, whereby a constant volume of the liquid sample is spread in a unit area of the spreading layer to feed a constant volume of the sample liquid to a unit area of the reaction layer 14 or the first reaction layer 24A.

The same materials used as the materials for the porous matrix, including fibrous and non-fibrous porous sheet materials, may also be used as the materials for the spreading layer. Particularly preferred are woven and knitted cloths.

This fifth embodiment provided with a spreading layer has the merits that the quantity of the spotted aqueous liquid sample need not be strictly controlled and that the analyzing operation can be further simplified.

Although separate reaction layer and coloring reagent layer are provided in the aforementioned embodiments, the reaction layer and the coloring reagent layer may be united into a single layer. For example, a cloth carrying an immobilized antibody (antigen) and an immobilized enzyme substrate may be impregnated with a hydrophilic polymer, such as gelatine, containing a detection reagent, or simply impregnated with a detection reagent to unify the reaction layer with the coloring reagent layer.

Although the processes and multi-layered elements for quantitative analysis of antigens have been described in the foregoing description, the present invention includes processes and multi-layered elements which are used for quantitative analysis of antibodies. When an antibody is the analyte immuno-reactant, an immobilized antigen is used in place of the immobilized antibody and a complex of an enzyme and the antibody is used in place of the antigen-enzyme complex in each of the aforementioned embodiments.

EXAMPLES OF THE INVENTION

The present invention will now be described more specifically with reference to examples thereof.

EXAMPLE 1

(1) Preparation of $T_4$-MEMIDA $T_4$ (thyroxine) was analyzed as the analyte antigen. In order to combine the low molecular weight $T_4$ with an enzyme, and to prepare the antibody for $T_4$ at a high efficiency, N-methyl-N-carboxymethylglycylthyroxine methyl ester ($T_4$-MEMIDA) waS prepared and then introduced with a spacer.

2g of thyroxinemethylester hydrochloride salt was dissolved in 15 ml of N,N-dimethylformamide (DMF) and then added with 500 microliters of triethylamine. While cooling the solution to $-15°$ C., 460 microliters of isobutyl chloroformate was added for reaction. After the lapse of 10 minutes, a solution of 0.55g of N-methylimino diacetate was added and then dissolved in 5 ml of tetrahydrofuran (THF), and the admixture was maintained at $0°$ C. for 10 minutes and then maintained at room temperature for an additional 30 minutes for reaction, and then the reaction system was concentrated under a reduced pressure. The residue was dissolved in 50 ml of THF, added with 150 ml of ethyl acetate, and then agitated by shaking. The ethyl acetate phase was fractionated. The fractionated ethyl acetate phase was rinsed with distilled water three times and then with a saturated aqueous solution of sodium chloride one time, and the thus rinsed ethyl acetate phase was dried with anhydrous sodium sulfate and concentrated under a reduced pressure. The residue was dissolved in 20 ml of THF, and added with a small quantity of n-hexane to obtain a crystal. The crystal was filtered off and dried under a reduced pressure to obtain 2.3g of a specimen (Yield: 69%).

(2) Preparation of Anti-$T_4$ (Thyroxine) Serum 100 mg of the $T_4$-MEMIDA prepared following to the procedure as described in the preceding paragraph (1) was dissolved in 2.0 ml of dry DMF, added with 15 mg of N-hydroxysuccinimide, and further added with 25 mg of 1-ethyl-3-(3-dimethylaminopropyl)carbodiimide (ECDI) on an ice bath to allow to react at $4°$ C. for one night. The reacted system was added dropwise into 20 ml of a 0.05M carbonate buffer solution (pH 9.0) containing 100 mg of a bovine serum albumin (Fraction V, produced by Miles Laboratories Inc.) on an ice bath for reaction. The reacted system was demineralized through dialysis with the same buffer solution for 2 days (2 liters$\times$4 times) and with distilled water for 2 days (2 liters$\times$4 times), and then freeze-dried to obtain 130 mg of a solid. The thus obtained solid was analyzed through the infrared spectometry. The solid was hydrolized with hydrochloric acid, and the hydrolyzed product was analyzed through the ultraviolet spectometry. In view of the results of the infrared and ultraviolet spectrometries, it was found that about twenty $T_4$-MEMIDA molecules were introduced to one bovine serum albumin molecule as the haptenes.

A rabbit was immunized with the dry solid prepared by the foregoing process and following to the ordinary treatment, and an anti-thyroxine (anti-$T_4$) serum was obtained from the rabbit.

(3) Preparation of T4-β-Galactosidase Complex 50 mg of the T4-MEMIDA prepared by the process as described in paragraph (1) was dissolved in 2 ml of DMF. The solution was cooled to −15° C. and added and mixed with 7 microliters of isobutyl chloroformate and 8 microliters of triethylamine. 2.0g of a β-D-galactosidase (originated from *E. Coli;* produced by Sigma Chemical Co.) was dissolved in 10 ml of a 50 mM carbonate buffer solution (pH 8.5), and added dropwise with the reaction product of T4-MEMIDA on an ice bath. After reacting for 2 hours, the reaction system was demineralized through dialysis with a 20 mM sodium carbonate buffer solution (pH 8.5) at 4° C. overnight, and then with distilled water for one day. The demineralized solution was applied to a chromatograph column using Sepharose CL-4B (produced by Farmacia Finechemicals Co., Ltd.) to obtain a T4-β-galactosidase fraction. A 50 mM phosphate buffer solution (pH 7.0) was used for elution.

(4) Preparation of Agarose Carrying to Immobilize Anti-T4 Antibody

On an ice bath, 1.5 ml of anti-thyroxine (T4) antiserum was added with 1 ml of a saturated ammonium sulfate solution to precipitate the IgG fraction. The precipitated IgG fraction was dialysed and then demineralized to obtain an anti-T4 antibody.

Sepharose was used as the agarose.

15g of Sepharose 4B (produced by Pharmacia Finechemicals Co., Ltd.) activated by CNBr was swelled by 100 ml of water, and then rinsed with 2 liters of 0.001 N hydrochloric acid on a glass filter. The IgG fraction of the anti-T4 antibody was dissolved in 30 ml of a 0.1 M bicarbonate buffer solution (pH 8.5; containing 0.5 M NaCl), and then added to the rinsed Sepharose 4B activated with CNBr, and reacted at 4° C. for 16 hours under agitation. After the completion of reaction, the reaction system was filtered through a glass filter, and 50 ml of a 1M ethanolamine (pH 8 to 8.5, adjusted with hydrochloric acid) was added to react again at 4° C. for 2 to 5 hours. The precipitate was rinsed on a glass filter alternately with a 0.1M acetate buffer solution (pH 4.0, containing 1M NaCl) and with a 0.1M borate buffer solution (pH 8.0, containing 1M NaCl) for three times each. After rinsing, the precipitate was suspended in a 0.1M glycine buffer solution (pH 9.0, containing 0.1M NaCl and 0.1% of sodium azide) so that 200 micrograms of dry agarose was contained in 1 ml of the suspension.

(5) Preparation of Agarose Carrying to Immobilize Galactose Oligomer

An oligomer of galactose was synthesized by the ordinary process ("Seikagaku Jikken Koza" (Biochemical Experiment Series), vol. 4, edited by Biochemical Society of Japan).

Generally following to the procedures as set forth in paragraph (4), the aforementioned oligomer was reacted with Sepharose 4B activated by CNBr to prepare a galactose oligomer immobilized by agarose (Sepharose). The reaction system was diluted with distilled water so that 200 micrograms of dry agarose was contained in 1 ml of the suspension.

(6) Analysis of T4

A coloring reagent solution and a sample liquid having, respectively, the following compositions were prepared.

Coloring Reagent Solution: A 0.1M Tris-HCl buffer solution (pH 6.5) containing the following ingredients of:

| Orthophenylenediamine | 2 mg/ml |
|---|---|
| $H_2O_2$ | 0.03% |

Sample Liquid: A 0.1M Tris-HCl buffer solution (pH 6.5) containing the following ingredients of:

| Human Serum Albumin (produced by Sigma Chemicals Co.) | 1 mg/ml |
|---|---|
| Sodium 1-Anilinonaphthalene-8-sulfonate | 1 mg/ml |
| T4-β-galactosidase | 10 μg/ml |
| T4 | 0 to 2 μg/ml |

A reaction liquid was prepared by mixing 2 ml of the suspension of the anti-T4 antibody immobilized by agarose as prepared by the paragraph (4), 2 ml of the suspension of the galactose oligomer immobilized by agarose as prepared by the paragraph (5), 0.5 ml of the coloring reagent solution and 0.5 ml of the sample liquid. A comparative reaction liquid was prepared by using an aqueous solution of galactose oligomer containing the same content of galactose oligomer in place of the suspension of the galactose oligomer immobilized by agarose.

The reaction liquid and the comparative reaction liquid were reacted at 25° C. for 60 minutes while mixing by repeated inversion. The reaction was terminated by the addition of 2 ml of a 2N sulfuric acid solution, and the precipitating proteins, agarose and other ingredients were separated by centrifugal separation (3,000 rpm, 20 minutes). The absorbance of the supernatant at the wavelength of 490 nm was measured. The results were shown in the following Table.

| Absorbance of Supernatant of the Reacted Liquids | | |
|---|---|---|
| Concentration of T4 in the Sample Liquid (μg/ml) | Reaction Liquid | Comparative Reaction Liquid |
| 0 | 0.35 | 0.68 |
| 0.04 | 0.38 | 0.69 |
| 0.12 | 0.42 | 0.70 |
| 0.36 | 0.48 | 0.70 |
| 2.0 | 0.52 | 0.72 |

As seen from the data set forth above, when both of the antibody and the enzyme substrate were immobilized, the enzyme activity of the antigen-enzyme complex was reduced, so that the antigen-enzyme complex (B) combined with the immobilized antibody could be microscopically detected as separated from the antigen-enzyme complex (F) which had not been combined with the antibody in the same solution even if they were not physically separated from each other.

It was also found that the analyte antigen could be detected by the difference in enzyme activity resulted from the competitive antigen-antibody reactions.

EXAMPLE 2

(1) Preparation of Detection Sheet (Coloring Reagent Layer)

A reagent layer for quantitative analysis of galactose was coated on a colorless and transparent polyethyleneterephthalate (PET) film having a thickness of 185 microns and applied with an undercoat for gelatine to form a coating having a thickness of about 15 microns. The composition of the reagent layer will be set forth below.

| Component | Part by Weight |
| --- | --- |
| Galactose Oxidase | 2 |
| Peroxydase | 1 |
| 1,7-Dihydroxynaphthalene | 5 |
| 4-Aminoantipyrine | 5 |
| Gelatine Treated with Alkali | 200 |
| Nonion HS 210 (Surfactant produced by Nippon Oils And Fats Co., Ltd.; Polyoxyethylene Octylphenyl Ether) | 2 |

A color shielding layer having a thickness in the dry state of about 15 microns was formed on the reagent layer by coating an aqueous suspension of a mixture containing 1 part by weight of dry gelatine and 8 parts by weight of microparticles of titanium dioxide. An overcoat layer having a thickness in the dry state of about 5 microns was formed on the color shielding layer by coating a gelatine solution containing 0.2% of a nonionic surfactant (HS 210) to prepare a detection sheet (coloring reagent layer).

(2) Preparation of Reaction Layer Sheet 2g of a glass fiber filter GA-100 (produced by Toyo Filter Co., Ltd.) was cut into 3 mm square pieces which were dispersed in 400 ml of water using a homogenizer (produced by Nippon Seiki Co., Ltd.; 15,000 rpm, 10 minutes). The dispersion was filtered successively through a stainless steel mesh of 2 m/m and a stainless steel mesh of 1 m/m. The glass fiber captured by the 1 m/m mesh were dispersed in 500 ml of a 0.1M glycine buffer solution (pH 9.0) containing 0.5M NaCl. A predetermined volume of the dispersion was filtered through a membrane filter to separate glass fibers. The buffer solution was drained from the separated glass fibers which were then dried and weighed to know the concentration of glass fibers (mg/ml) dispersed in the buffer solution.

A calculated volume of the dispersion containing 30 mg of glass fibers was placed in a beaker to which admixed were 1 ml of the suspension of the anti-$T_4$ antibody immobilized by agarose, as prepared in step (4) of Example 1, and 1 ml of the suspension of galactose oligomer immobilized by agarose, as prepared in step (5) of Example 1. The admixture was spread over a membrane filter (HAWP Filter produced by Millipore Corporation; Pore Size: 0.45 microns; 47 mm$\phi$) to make a sheet which was used as a reaction layer sheet (reaction layer).

A comparative reaction layer sheet was prepared by using agarose (Sepharose 4B) in place of agarose carrying the anti-$T_4$ antibody.

(3) Preparation of Multi-Layered Element

A 12 mm diameter disk was cut from each of the detection sheet and the reaction layer sheet, prepared respectively in steps (1) and (2). The disk of the detection sheet was overlaid on the PET film surface and the disk of the reaction layer sheet was overlaid on the detection sheet. Thus, a multi-layered element was prepared.

A comparative multi-layered element was prepared using the comparative reaction layer sheet.

(4) Determination of $T_4$

A sample liquid was prepared by adding the following ingredients to a 0.1M glycine buffer solution (pH 8).

| | |
| --- | --- |
| Human Serum Albumin (produced by Sigma Chemical Co.) | 1 mg/ml |
| Sodium 1-Anilinonaphthalene-8-sulfonate | 1 mg/ml |
| $T_4$-$\beta$-galactosidase Complex | 50 $\mu$g/ml |
| $T_4$ | 0 to 10 $\mu$g/ml |

100 microliters of the sample liquid was spotted on the multi-layered element prepared in step (3) and incubated at 37° C. for 8 minutes. The multi-layered element was irradiated by a visible light having a center wavelength of 500 nm from the PET film side, and the optical density of the reflected light was measured.

Figure 3:
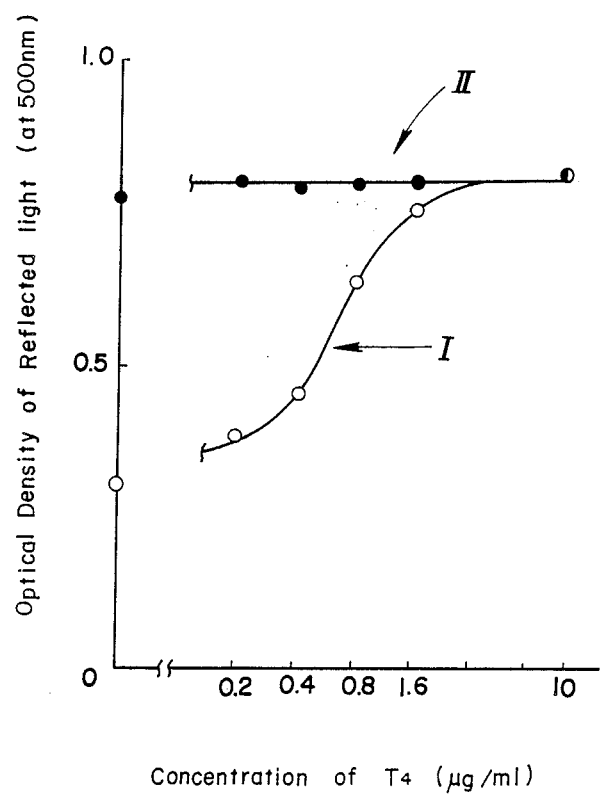
FIG. 3 is a graph showing the results of analyses conducted by the use of an embodiment of the multi-layered element of this invention and a comparative multi-layered element.

The results of the measurements are shown in FIG. 3. As shown by the curve I in the Figure, the optical density of the reflected light is changed in response to the change in concentration of $T_4$ when the multi-layered element of this embodiment is used, curve I being adapted for use as a calibration curve. It should be appreciated that $T_4$ could be determined within a very short time without the need of B/F separation by the use of a multi-layered element prepared in accordance with this invention. It should also be appreciated that the multi-layered element of this invention has a detection sensitivity superior over the sensitivity of the conventional method, since the enzyme activity per se is utilized for the determination rather than measuring a depression rate of the enzyme activity.

The curve II (plotting the black marks) in FIG. 3 shows the results of an experiment wherein the comparative multi-layered element is used.

As should be appreciated from the foregoing that the present invention provides a multi-layered element for quantitative analysis of an analyte antigen (or antibody). The analyte antigen (or analyte antibody) is mixed with an enzyme-labelled antigen (or enzyme-labelled antibody). The element has a reaction layer in which a specific antibody (or antigen) for the analyte antigen (or analyte antibody) is carried by a first carrier to be immobilized thereby. The reaction layer further contains an enzyme substrate immobilized by a second carrier which is different from the first carrier. When the mixture of the analyte antigen and the enzyme-labelled antigen (or mixture of the analyte antibody and the enzyme-labelled antibody) penetrates into the reaction layer, competitive reactions take place so that only the part of the enzyme-labelled antigen (or enzyme-labelled antibody) which has not been combined with the immobilized antibody (or immobilized antigen) reacts with the immobilized enzyme substrate to produce an enzymatic reaction product which is detected by the detection composition contained in the reagent layer. Accordingly, the analyte antigen (or analyte antibody) can be quantitatively analyzed in a simple manner within a short time using a very small quantity of liquid sample.

What is claimed is:

1. A multi-layered analytical element for the quantitative analysis of an analyte antigen, mixed with an enzyme-labelled antigen in a sample, comprising:
   a water-impermeable and light-transmissible support;
   a reagent layer carried by said support and containing a hydrophilic polymer as a binder; and a reaction layer covering said reagent layer and made of a porous matrix;

said reaction layer containing an antibody for the antigen and a substrate for the enzyme of the enzyme labelled antigen, said antibody being immobilized by a first water-insoluble carrier, said substrate being immobilized by a second water-insoluble carrier which is different from said first water-insoluble carrier;

said reagent layer containing a detection reagent composition for coupling with an enzymatic reaction product produced from the reaction of the enzymatic label and substrate therefor to develop a measurable color.

2. The multi-layered element for the quantitative analysis of an analyte antigen as claimed in claim 1, wherein said reaction layer further contains said enzyme-labelled antigen so that analyte antigen in the sample is mixed with said enzyme-labelled antigen therein.

3. The multi-layered element for the quantitative analysis of an analyte antigen as claimed in claim 1, wherein said reagent layer further contains said enzyme-labelled antigen so that analyte antigen in the sample is mixed with said enzyme-labelled antigen therein.

4. The multi-layered element for the quantitative analysis of an analyte antigen as claimed in claim 1, wherein said reaction layer is covered by a spreading layer containing said enzyme-labelled antigen so that analyte antigen in the sample is mixed with enzyme-labelled antigen in said spreading layer.

5. The multi-layered element for the quantitative analysis of an analyte antigen as claimed in claim 1, 3 or 4, wherein said reaction layer comprises a first reaction layer containing said antibody immobilized by said first water-insoluble carrier and a second reaction layer containing said enzyme substrate immobilized by said second water-insoluble carrier, and wherein said second reaction layer covers said reagent layer and said first reaction layer covers said second reaction layer.

6. The multi-layered element for the quantitative analysis of an analyte antigen as claimed in claim 2, wherein said reaction layer comprises:

a first reaction layer containing said antibody immobilized by said first water-insoluble carrier, and said enzyme-labelled antigen; and a second reaction layer containing said enzyme substrate immobilized by said second water-insoluble carrier;

said second reaction layer covering said reagent layer, and said first layer covering said second reaction layer.

7. The multi-layered element for the quantitative analysis of an analyte antigen as claimed in claim 1, 2, 3, or 4, wherein said reaction layer further contains micro particles for shielding colors.

8. The multi-layered element for the quantitative analysis of an analyte antigen as claimed in claim 5 wherein said second reaction layer further contains micro particles for shielding colors 9. The multi-layered element for the quantitative analysis of an analyte antigen as claimed in claim 1, 2, 3, or 4, wherein said porous matrix is a fibrous material.

10. The multi-layered element for the quantitative analysis of an analyte antigen as claimed in claim 1, 2, 3, or 4, wherein said porous matrix is a non-fibrous material.

11. The multi-layered element for the quantitative analysis of an analyte antigen as claimed in claim 1, 2, 3, or 4, wherein said porous matrix is composed of said water-soluble carrier.

12. The multi-layered element for the quantitative analysis of an analyte antigen as claimed in claim 6, wherein said second reaction layer further contains micro particles for shielding colors.

13. A multi-layered element for the quantitative analysis of an analyte antibody, mixed with an enzyme-labelled antibody in a sample, comprising:

a water-impermeable and light-transmissible support;

a reagent layer carried by said support and containing a hydrophilic polymer as a binder; and a reaction layer covering said reagent layer and made of a porous matrix;

said reaction layer containing an antigen for the antibody and a substrate for the enzyme of the enzyme-labelled antibody, said antigen being immobilized by a first water-soluble carrier, said substrate being immobilized by a second water-insoluble carrier which is different from said first water-insoluble carrier;

said reagent layer containing a detection reagent composition for coupling with an enzymatic reaction product produced from the reaction of the enzymatic label and substrate therefor to develop a measurable color.

14. The multi-layered element for the quantitative analysis of an analyte antibody as claimed in claim 13, wherein said reaction layer further contains said enzyme-labelled antibody so that analyte antibody in the sample is mixed with said enzyme-labelled antibody therein.

15. The multi-layered element for the quantitative analysis of an analyte antibody as claimed in claim 13, wherein said reagent layer further contains said enzyme-labelled antibody so that analyte antibody in the sample is mixed with said enzyme-labelled antibody therein.

16. The multi-layered element for the quantitative analysis of an analyte antibody as claimed in claim 13, wherein said reaction layer is covered by a spreading layer containing said enzyme-labelled antibody so that analyte antibody in the sample is mixed with enzyme-labelled antibody in said spreading layer.

17. The multi-layered element for the quantitative analysis of an analyte antibody as claimed in claim 13, 14, or 16, wherein said reaction layer comprises a first reaction layer containing said antigen immobilized by said first water-insoluble carrier and a second reaction layer containing said enzyme substrate immobilized by said second water-insoluble carrier, and wherein said second reaction layer covers said reagent layer and said first reaction layer covers said second reaction layer.

18. The multi-layered element for the quantitative analysis of an analyte antibody as claimed in claim 14, wherein said reaction layer comprises:

a first reaction layer containing said antigen immobilized by said first water-insoluble carrier, and said enzyme-labelled antibody; and a second reaction layer containing said enzyme substrate immobilized by said second water-insoluble carrier;

said second reaction layer covering said reagent layer, and said first layer covering said second reaction layer.

19. The multi-layered element for the quantitative analysis of an analyte antibody as claimed in any claim 14, 15, or 16, wherein said reaction layer further contains micro particles for shielding colors.

20. The multi-layered element for the quantitative analysis of an analyte antibody as claimed in claim 17 wherein said second reaction layer further contains micro particles for shielding colors.

21. The multi-layered element for the quantitative analysis of an analyte antibody as claimed in claim 14, 15, or 16, wherein said porous matrix is a fibrous material.

22. The multi-layered element for the quantitative analysis of an analyte antibody as claimed in claim 14, 15, or 16, wherein said porous matrix is a non-fibrous material.

23. The multi-layered element for the quantitative analysis of an analyte antibody as claimed in claim 14, 15, or 16, wherein said porous matrix is composed of said water-insoluble carrier.

24. The multi-layered element for the quantitative analysis of an analyte antibody as claimed in claim 18, wherein said second reaction layer further contains micro particles for shielding colors.

* * * * *